United States Patent
Matsumura et al.

(10) Patent No.: US 10,149,661 B2
(45) Date of Patent: Dec. 11, 2018

(54) PROBE COVER, ULTRASONIC PROBE, AND ULTRASONIC IMAGE DISPLAY APPARATUS

(71) Applicant: GE MEDICAL SYSTEMS GLOBAL TECHNOLOGY COMPANY, LLC, Waukesha, WI (US)

(72) Inventors: Kiyoshi Matsumura, Tokyo (JP); Mitsuhiro Nozaki, Tokyo (JP)

(73) Assignee: GE Medical Systems Global Technology, Waukesha, WI (US)

( * ) Notice: Subject to any disclaimer, the term of this patent is extended or adjusted under 35 U.S.C. 154(b) by 367 days.

(21) Appl. No.: 13/629,352

(22) Filed: Sep. 27, 2012

(65) Prior Publication Data
US 2013/0085391 A1   Apr. 4, 2013

(30) Foreign Application Priority Data
Sep. 29, 2011 (JP) ................................ 2011-214191

(51) Int. Cl.
*A61B 8/00* (2006.01)

(52) U.S. Cl.
CPC .......... *A61B 8/4455* (2013.01); *A61B 8/4411* (2013.01)

(58) Field of Classification Search
USPC .......................... 600/407, 437, 446, 459, 462
See application file for complete search history.

(56) References Cited

U.S. PATENT DOCUMENTS

| | | | |
|---|---|---|---|
| 5,334,963 A * | 8/1994 | Wessling | 335/2 |
| 5,953,795 A * | 9/1999 | Bauer | 24/303 |
| 6,132,378 A | 10/2000 | Marino | |
| 6,267,726 B1 | 7/2001 | Grimm | |
| 6,402,695 B1 | 6/2002 | Grimm | |
| 6,645,148 B2 * | 11/2003 | Nguyen-Dinh et al. | 600/459 |
| 6,800,987 B2 | 10/2004 | Toda | |
| 7,135,809 B2 | 11/2006 | Ossmann | |
| 2003/0031591 A1 * | 2/2003 | Whitson | G01N 33/4875 422/50 |
| 2005/0126897 A1 * | 6/2005 | Stephens | H01H 13/04 200/5 A |
| 2008/0077198 A1 * | 3/2008 | Webb et al. | 607/88 |
| 2010/0004543 A1 | 1/2010 | Ahlund et al. | |
| 2010/0305450 A1 | 12/2010 | Kosaku | |
| 2011/0113886 A1 | 5/2011 | Elejalde et al. | |
| 2011/0166484 A1 | 7/2011 | Virta | |
| 2011/0228458 A1 * | 9/2011 | Richardson et al. | 361/679.01 |

FOREIGN PATENT DOCUMENTS

| | | |
|---|---|---|
| JP | H06007387 U | 1/1994 |
| JP | 11-056852 | 3/1999 |
| JP | 2001135192 | 5/2001 |
| JP | 2002-301075 | 10/2002 |
| JP | 2003135455 | 5/2003 |
| WO | 2007088642 | 8/2007 |

OTHER PUBLICATIONS

JPO Office Action for related application JP2011-214191 dated Aug. 25, 2014.

* cited by examiner

*Primary Examiner* — Tse Chen
*Assistant Examiner* — Jason Ip

(57) ABSTRACT

A probe cover is provided. The probe cover is configured to be detachably attached to an ultrasonic probe and cover plural switches on a surface of the ultrasonic probe, the probe cover including a depression portion by which an operator can depress at least some of the plural switches when the probe cover is attached to the ultrasonic probe.

16 Claims, 18 Drawing Sheets

PROBE COVER, ULTRASONIC PROBE, AND ULTRASONIC IMAGE DISPLAY APPARATUS

CROSS REFERENCE TO RELATED APPLICATIONS

This application claims the benefit of Japanese Patent Application No. 2011-214191 filed Sep. 29, 2011, which is hereby incorporated by reference in its entirety.

BACKGROUND OF THE INVENTION

The present invention relates to a probe cover attached to an ultrasonic probe, an ultrasonic probe, and an ultrasonic image display apparatus.

An ultrasonic image display apparatus displays an ultrasonic image based upon an echo signal obtained by performing ultrasonic scan to a subject. In the ultrasonic image display apparatus described above, the ultrasonic scan is performed by use of an ultrasonic probe connected to a body of the apparatus through a probe cable.

In an ultrasonic diagnostic apparatus that displays an ultrasonic image such as a B-mode image to makes a diagnosis, a freezing operation of the ultrasonic image or a recording operation of the ultrasonic image is sometimes performed during the scan. In this case, an operator holds the ultrasonic probe with his/her one hand, and with this state, he/she operates an operation unit on the apparatus body with his/her other hand. However, there may be a case where the operation unit is difficult to operate with his/her other hand. In view of this, JP-A No. 2002-301075 describes an ultrasonic probe provided with a switch. The operator can depress the switch with the hand holding the ultrasonic probe, thereby being capable of operating the ultrasonic probe.

The hand holding the ultrasonic probe may be changed depending upon a region to be examined and an examination purpose. The position of the switch for which the operator can easily depress the switch is different between the case in which the operator holds the ultrasonic probe with his/her right hand and the case in which the operator holds the ultrasonic probe with his/her left hand. Therefore, an ultrasonic probe is considered that has switches on both a position for easy operation when he/she holds the probe with his/her right hand, and a position for easy operation when he/she holds the probe with his/her left hand. However, when the switches are provided on the positions described above, the switch that is not used by the hand holding the ultrasonic probe might involuntarily be depressed. Therefore, it has been demanded that the ultrasonic probe has switches on better positions for a right hand and left hand, and involuntary depression of the switches can be prevented.

BRIEF DESCRIPTION OF THE INVENTION

In one aspect, a probe cover is provided. The probe cover is detachably attached to an ultrasonic probe provided with plural switches on its surface, and covers the switches, the probe cover including a depression portion by which an operator can depress the switches in a state in which the probe cover is attached to the ultrasonic probe.

In another aspect, a probe cover is provided. The probe cover is detachably attached to an ultrasonic probe provided with plural switches on its surface, and covers the switches, the probe cover including an opening portion from which some of the plural switches are exposed.

In yet another aspect, a probe cover is provided. The probe cover includes a switch, and a transmission unit that wirelessly transmits a signal when the switch is depressed, the probe cover being detachably attached to an ultrasonic probe.

According to one aspect, in the ultrasonic probe to which the probe cover provided with the depression portion is attached, the switch is depressed by depressing the depression portion. The operator attaches the probe cover to the ultrasonic probe such that the depression portion is located on the switch to be used. Therefore, the position of the switch can be changed by the mounting manner of the probe cover. Accordingly, the switch that can be used can be located on both the position in which the operator can easily operate the switch with his/her right hand and the position in which the operator can easily operate the switch with his/her left hand. On the other hand, the switch that is not used is covered by the probe cover, which can prevent the switch from being involuntarily depressed.

According to another aspect, in the ultrasonic probe to which the probe cover formed with the opening portion is attached, the switch that is exposed from the opening portion can be depressed. The operator attaches the probe cover to the ultrasonic probe such that the opening portion is located on the switch to be used. Therefore, the position of the switch can be changed by the mounting manner of the probe cover. Accordingly, the switch that can be used can be located on both the position in which the operator can easily operate the switch with his/her right hand and the position in which the operator can easily operate the switch with his/her left hand. On the other hand, the switch that is not used is covered by the probe cover, which can prevent the switch from being involuntarily depressed.

According to still another aspect, the operator attaches the probe cover provided with the switch such that the switch is located on the desired position. Accordingly, the switch that can be used can be located on both the position in which the operator can easily operate the switch with his/her right hand and the position in which the operator can easily operate the switch with his/her left hand. On the other hand, only the switch that is to be used is provided. Therefore, there is no chance that the switch is involuntarily depressed.

DETAILED DESCRIPTION OF THE INVENTION

Exemplary embodiments will be described below.

First Embodiment

Figure 1:
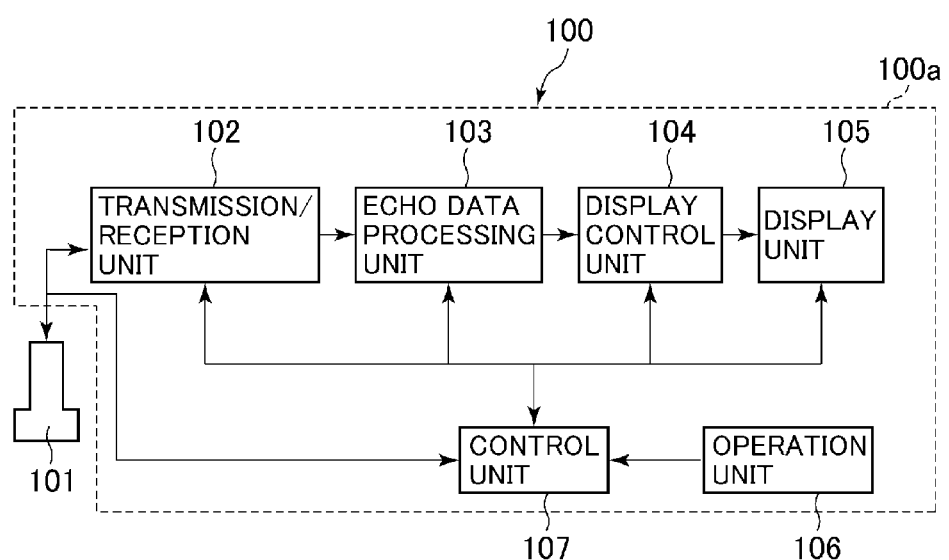
FIG. 1 is a block diagram illustrating one example of an ultrasonic diagnostic apparatus.

A first embodiment will firstly be described with reference to FIGS. 1 to 8. An ultrasonic diagnostic apparatus 100 illustrated in FIG. 1 is one example of an ultrasonic image display apparatus, and includes an ultrasonic probe 101, a transmission/reception unit 102, an echo data processing unit 103, a display control unit 104, a display unit 105, an operation unit 106, and a control unit 107. The transmission/reception unit 102, the echo data processing unit 103, the display control unit 104, the display unit 105, the operation unit 106, and the control unit 107 are provided in an apparatus body 100a. The ultrasonic probe 101 is connected to the apparatus body 100a via a probe cable 108 (see FIG. 2). A probe cover 1 (not illustrated in FIG. 1) is detachably mounted to the ultrasonic probe 101.

The ultrasonic probe 101 performs ultrasonic scan to a subject from plural ultrasonic vibrators (not illustrated). The ultrasonic probe 101 receives an ultrasonic echo signal.

Figure 2:
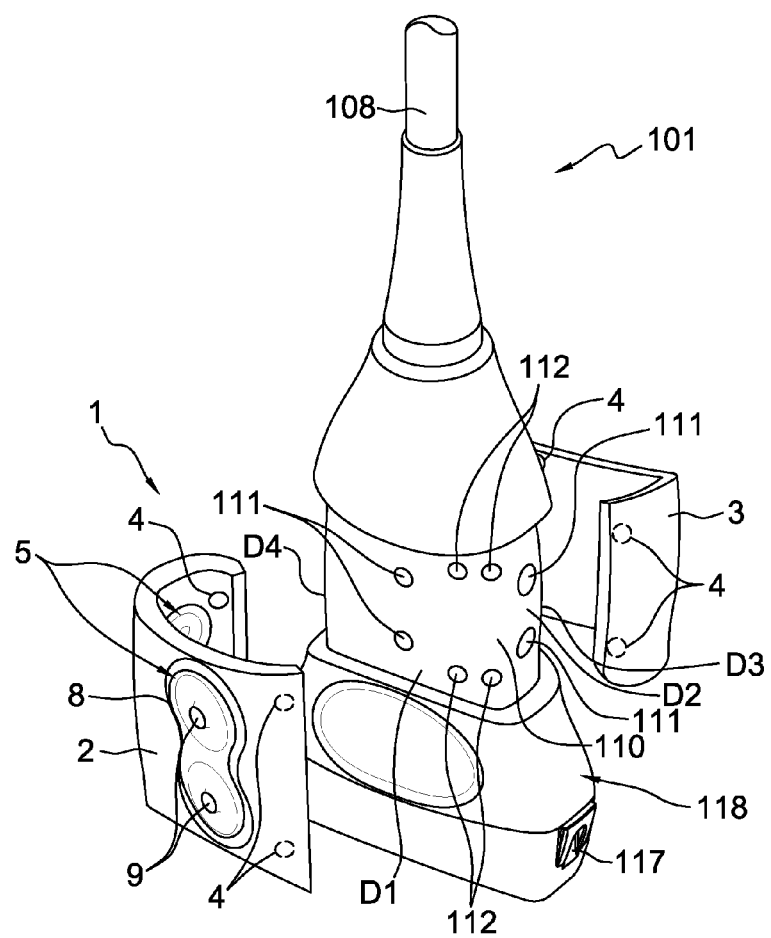
FIG. 2 is a perspective view illustrating an ultrasonic probe and a probe cover in the ultrasonic diagnostic apparatus illustrated in FIG. 1.

As illustrated in FIG. 2, the ultrasonic probe 101 has almost a rectangular shape in section, and is formed with a recess 110 with a predetermined width all over four surfaces of D1, D2, D3, and D4. The probe cover 1 is attached to the recess 110. Switches 111 and magnets 112 are provided on the recess 110.

The surfaces D1 and D3 are wide surfaces of the ultrasonic probe 101, while the surfaces D2 and D4 are narrow surfaces of the ultrasonic probe 101.

Two switches 111 are provided on each of the surfaces D1 to D4. Since the switches 111 are provided on the respective surfaces D1 to D4 as described above, the ultrasonic probe 101 is easily operated, even if an operator holds the probe with his/her right hand or left hand.

When the switches 111 are depressed, a signal is inputted to the control unit 107 through the probe cable 108 from the ultrasonic probe 101. The switches 111 are operation switches from which an instruction of the operator is inputted. A freezing operation of an ultrasonic image or a recording operation of the ultrasonic image is performed, for example, through a depression of the switches 111.

Figure 3:
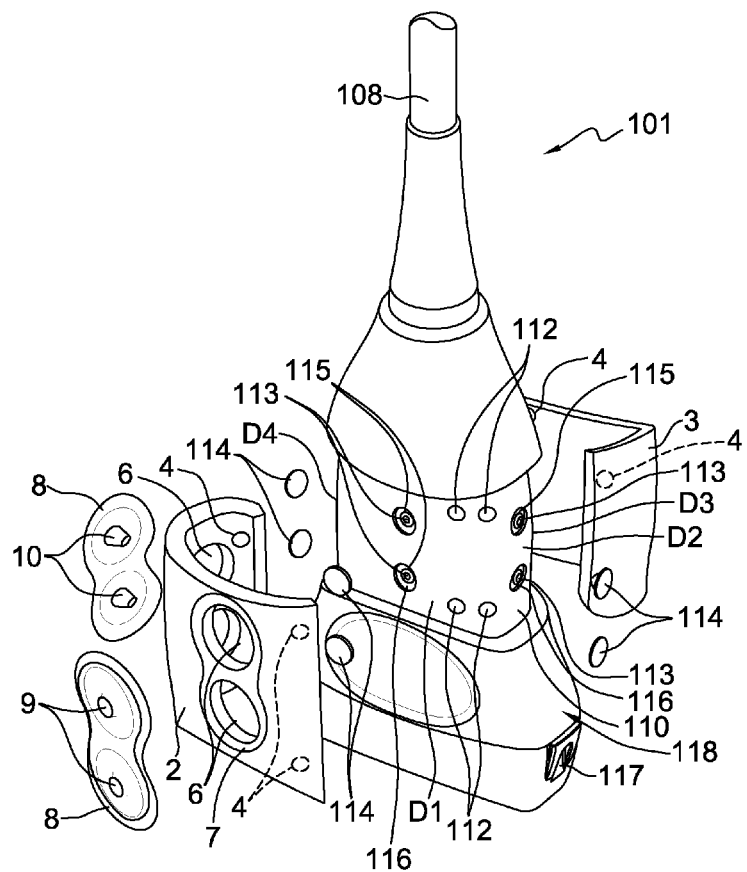
FIG. 3 is an exploded perspective view illustrating the ultrasonic probe and the probe cover in the ultrasonic diagnostic apparatus illustrated in FIG. 1.
Figure 4:
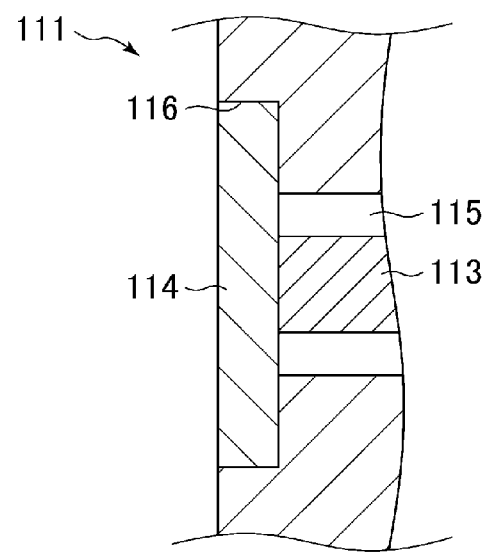
FIG. 4 is a partially enlarged sectional view of a switch provided to the ultrasonic probe.

As illustrated in FIGS. 3 and 4, each of the switches 111 is composed of a button 113 and an elastic plate 114. The button 113 is provided in a hole 115 formed in the recess 110. A circular recess 116 is formed around the hole 115. The circular recess 116 has a diameter same as that of the elastic plate 114, wherein the elastic plate 114 is mounted in the circular recess 116. The elastic plate 114 is fixed to the circular recess 116 with an adhesive agent in a liquid-tight manner, whereby the invasion of liquid into the hole 115 is prevented by the elastic plate 114.

Figure 5:
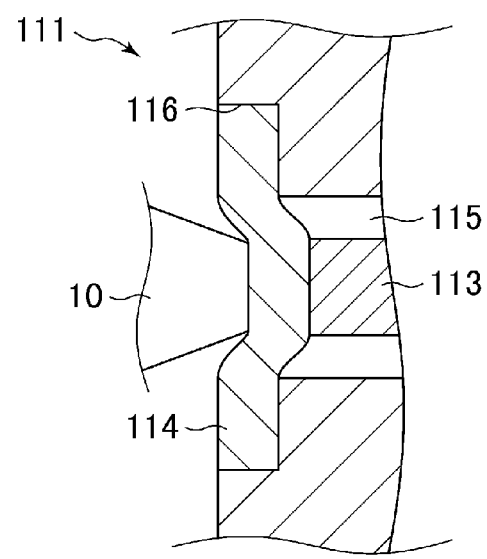
FIG. 5 is a sectional view illustrating a state in which an elastic plate is pressed by a convex portion to be elastically deformed from the state illustrated in FIG. 4, by which a button is depressed.

As illustrated in FIG. 5, when the elastic plate 114 provided in the circular recess 116 is pressed by a later-described projecting portion 10 on the probe cover 1, it is elastically deformed to depress the button 113. A signal is outputted to the control unit 107, when this button 113 is depressed.

The magnet 112 is provided on the surface of the recess 110. The magnet 112 is provided just below a magnet 4 provided on the probe cover 1 in a state in which the probe cover 1 is attached to the recess 110.

It is to be noted that numeral 117 denotes a locked portion for allowing a puncture adaptor (not illustrated), which is used to mount a puncture needle to the ultrasonic probe 101, to be locked. The operator makes an ultrasonic scan such that the side 118 of the ultrasonic probe 101 on which the locked portion 117 is formed always directs in a constant direction with respect the operator. Accordingly, there is no chance that the direction of the ultrasonic probe 101 is different between the case in which the operator holds the ultrasonic probe 101 with his/her right hand and the case in which the operator holds the ultrasonic probe 101 with his/her left hand.

The transmission/reception unit 102 supplies an electric signal, which is for transmitting ultrasonic wave under a predetermined scan condition from the ultrasonic probe 101, to the ultrasonic probe 2 based upon a control signal from the control unit 107. The transmission/reception unit 102 also performs a signal processing, such as an A/D conversion or phasing/adding process, to an echo signal received by the ultrasonic probe 101.

The echo data processing unit 103 performs a process for generating an ultrasonic image to echo data outputted from the transmission/reception unit 102. For example, the echo data processing unit 103 performs a B-mode process, such as a logarithmic compression process or envelope demodulation process, thereby generating B-mode data.

The display control unit 104 performs a scan conversion to the data inputted from the echo data processing unit 103 by use of a scan converter, so as to generate ultrasonic image data, and allows the display unit 105 to display the ultrasonic image based upon the ultrasonic image data. The display control unit 104 generates B-mode image data based upon the B-mode data, and displays the B-mode image on the display unit 105, for example.

The display unit 105 is made of an LCD (Liquid Crystal Display) or CRT (Cathode Ray Tube), for example. The operation unit 106 includes a switch, a keyboard, and a pointing device (not illustrated) used by the operator to input an instruction or information.

The control unit 107 is configured to include a CPU (Central Processing Unit), although not particularly illustrated. The control unit 107 reads a control program stored in a storage unit, not illustrated, and executes functions of respective units in the ultrasonic diagnostic apparatus 100.

The probe cover 1 will be described with reference to FIGS. 2, 3, and 6. The probe cover 1 is attached to the recess 110 of the ultrasonic probe 101 to cover the switches 111. More specifically, the probe cover 1 is made of a hard plastic. In the present embodiment, the probe cover 1 includes a first member 2 and a second member 3. The first member 2 and the second member 3 are formed to have almost an L-shape that can be fitted to the recess 110.

Two magnets 4 are provided on each of the first member 2 and the second member 3 at the end in the widthwise direction (a part thereof is not illustrated). The first member 2 and the second member 3 are detachably mounted to the ultrasonic probe 101 by the magnets 4 and the magnets 112 provided on the ultrasonic probe 101.

Figure 6:
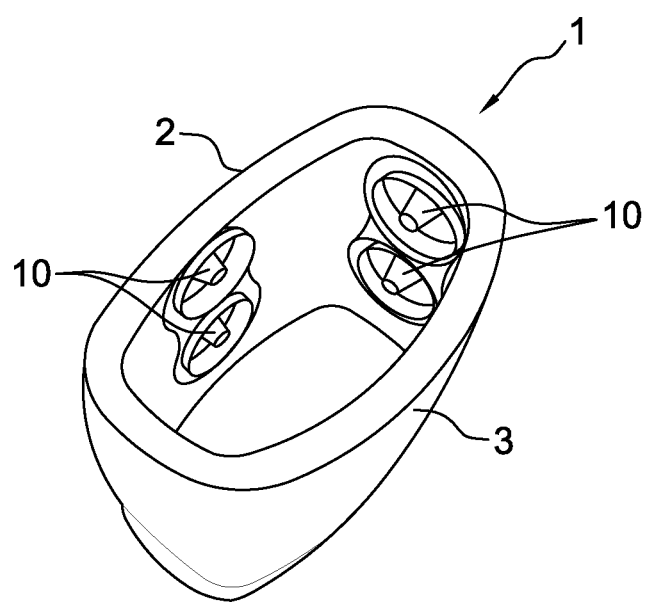
FIG. 6 is a perspective view illustrating the probe cover.

FIG. 6 illustrates that the ends of the first member 2 and the second member 3 in the widthwise direction are joined. The first member 2 and the second member 3 are attached to the ultrasonic probe 101 in the state illustrated in FIG. 6.

Plural depression portions 5 are provided on the first member 2. In the present embodiment, the depression portions 5 are provided on two places. Each of the depression portions 5 is provided on the position where the depression portion 5 can be located immediately above the switch 111 when the first member 2 is attached to the ultrasonic probe 101. The depression portion 5 is one example of an embodiment of the depression portion.

The depression portion 5 will further be described in detail. Through-holes 6 are formed on the depression portion 5 of the first member 2, wherein a recess 7 is formed around the through-holes 6. A depression plate 8 is provided on the recess 7 by an adhesive agent. The depression plate 8 is formed with convex portions 9 on its surface, while projecting portions 10 are formed on its back surface as illustrated in FIG. 6. The projecting portions 10 are formed on the positions corresponding to the convex portions 9. The convex portions 9 and the projecting portions 10 are located in the through-holes 6 when the depression plate 8 is attached to the recess 7.

The depression plate 8 is made of a material that can be elastically deformed. When the convex portion 9 is depressed, the depression plate 8 is elastically deformed to move the projecting portion 10. Therefore, when the convex portion 9 is depressed, the switch 111 is depressed.

When the ultrasonic scan is performed by use of the ultrasonic probe 101 according to the present embodiment, the operator attaches the first member 2 to the ultrasonic probe 101 in order that the depression portion 5 is located on the switch 111 (not illustrated in FIGS. 7 and 8) that is located on a place where the operator can easily depress with his/her hand holding the ultrasonic probe 101. The operator also attaches the second member 3 on the switch 111 that is not used.

Figure 7:
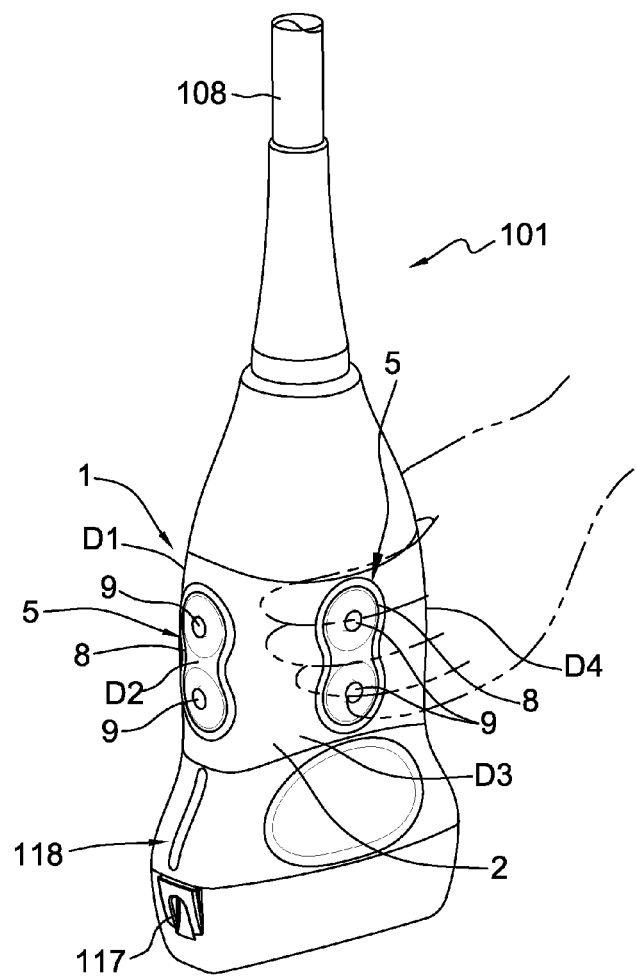
FIG. 7 is a perspective view illustrating the ultrasonic probe to which the probe cover is attached.
Figure 8:
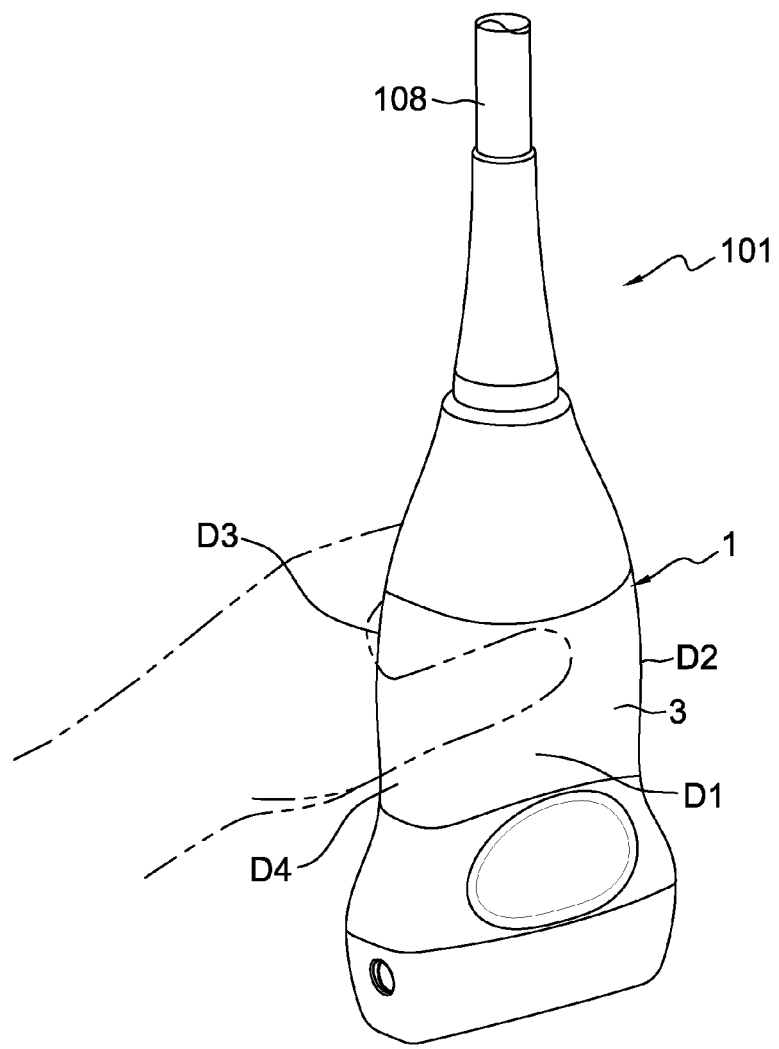
FIG. 8 is a perspective view of the ultrasonic probe illustrated in FIG. 7 as viewed from the reverse side.

FIGS. 7 and 8 illustrate that the operator holds the wide surfaces D1 and D3 of the ultrasonic probe 101 with his/her left hand. More specifically, the operator holds the ultrasonic probe 101 with his/her left hand in such a manner that his/her thumb is on the surface D1, and his/her other fingers are on the surface D3. In this case, the operator depresses the depression portion 5 provided on the surface D3 with his/her middle finger or annular finger, thereby depressing the switch 111.

When the operator holds the narrow surfaces D2 and D4 of the ultrasonic probe 101 with his/her left hand in case where the probe cover 1 is attached in the state illustrated in FIGS. 7 and 8, the operator depresses the depression portion 5 provided on the surface D2 with his/her middle finger or annular finger, thereby depressing the switch 111.

As described above, according to the first embodiment, the position where the first member 2 is attached and the position where the second member 3 is attached to the ultrasonic probe 101 can be changed, whereby the position of the switch 111 that can be used (the switch 111 that can be depressed by the depression portion 5) can be changed. Therefore, the switch 111 that can be used can be located on both of the position where the operator can easily operate the switch 111 with his/her right hand and the position where the operator can easily operate the switch 111 with his/her left hand. On the other hand, the switch 111 that is not used is covered by the second member 3 of the probe cover 1, which can prevent the switch 111 from involuntarily being depressed.

Figure 9:
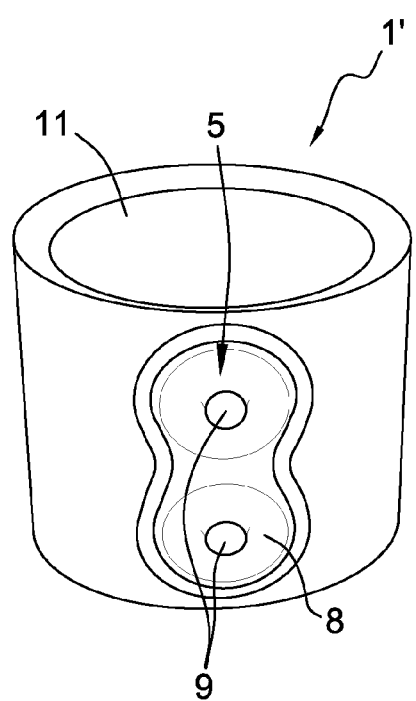
FIG. 9 is a perspective view illustrating a probe cover according to a modification of the first embodiment.
Figure 10:
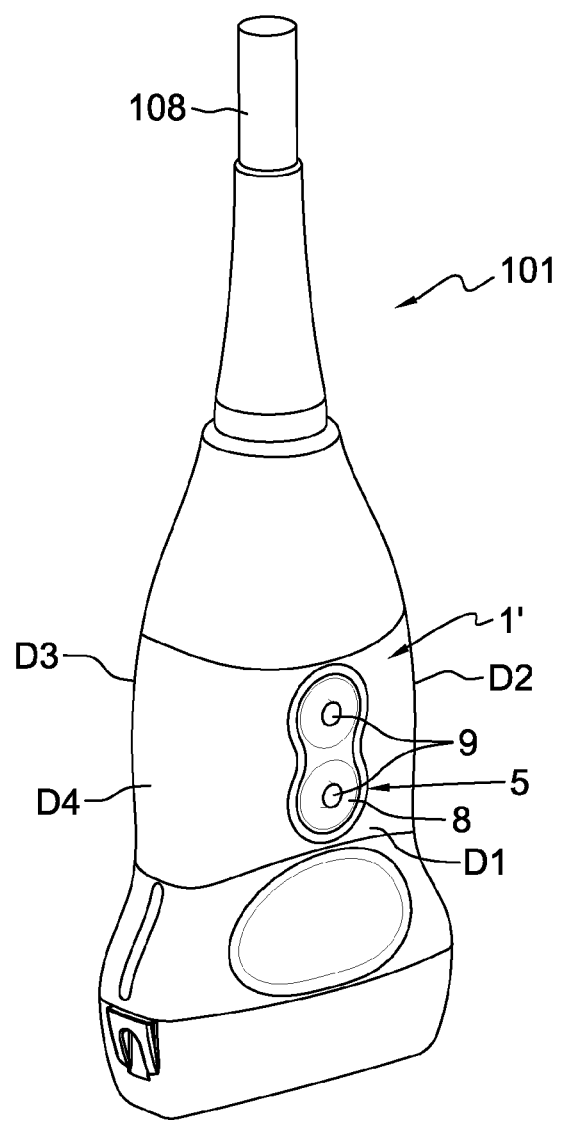
FIG. 10 is a perspective view illustrating an ultrasonic probe to which the probe cover illustrated in FIG. 9 is attached.

A modification of the first embodiment will next be described. A probe cover 1' illustrated in FIG. 9 does not include the first member 2 and the second member 3, but is annularly formed from a material that is elastically deformed (for example, elastomer). In the probe cover 1', the depression plate 8 is integrally formed with the cover body. The depression portion 5 is provided on only one place. As illustrated in FIG. 10, the probe cover 1' is attached in order that the depression portion 5 is located immediately above the switch 111 to be used (not illustrated in FIG. 10). The probe cover 1' is put on the ultrasonic probe 101 from the opening 11 due to the elastic deformation, and is attached to the recess 110 (not illustrated in FIG. 10).

In the present embodiment, the magnet 112 is not provided on the ultrasonic probe 101. The probe cover 1' is held by the recess 110 of the ultrasonic probe 101 by the elasticity.

Figure 11:
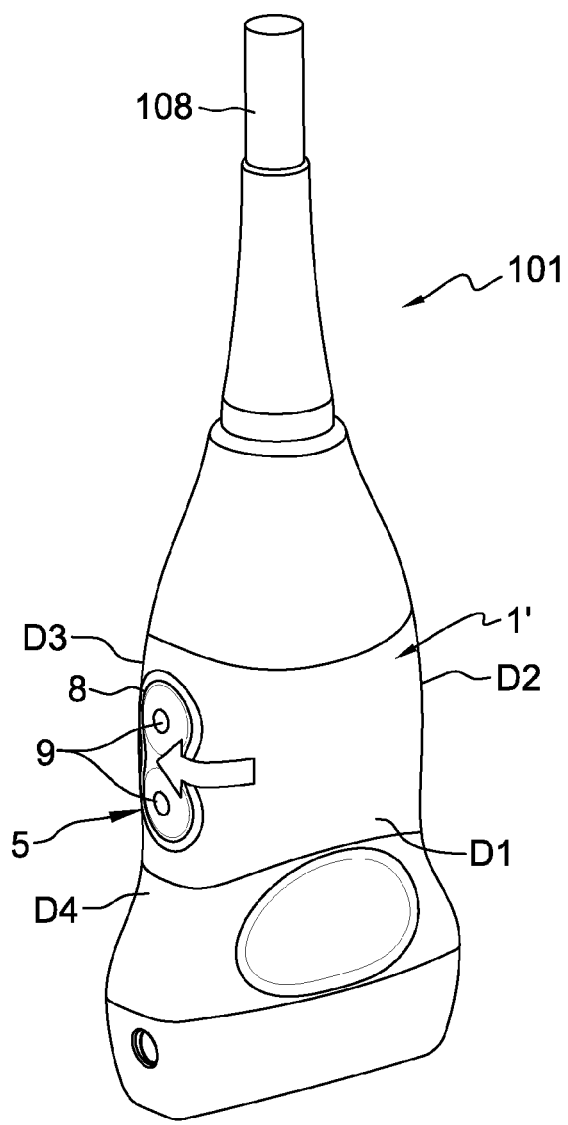
FIG. 11 is a perspective view illustrating the ultrasonic probe in which a depression portion of the probe cover is moved from the state illustrated in FIG. 10.

In FIG. 10, the depression portion 5 is located immediately above the switch 111 (not illustrated in FIG. 10) provided on the wide surface D1. When the switch 111 provided on the narrow surface D4 is intended to be used, for example, the depression portion 5 is moved in a direction of an arrow, as shown in FIG. 11, by elastically deforming the probe cover 1', so as to allow the depression portion 5 to be located on the narrow surface D4.

Second Embodiment

A second embodiment will next be described. The components same as those in the first embodiment are identified by the same numerals.

Figure 12:
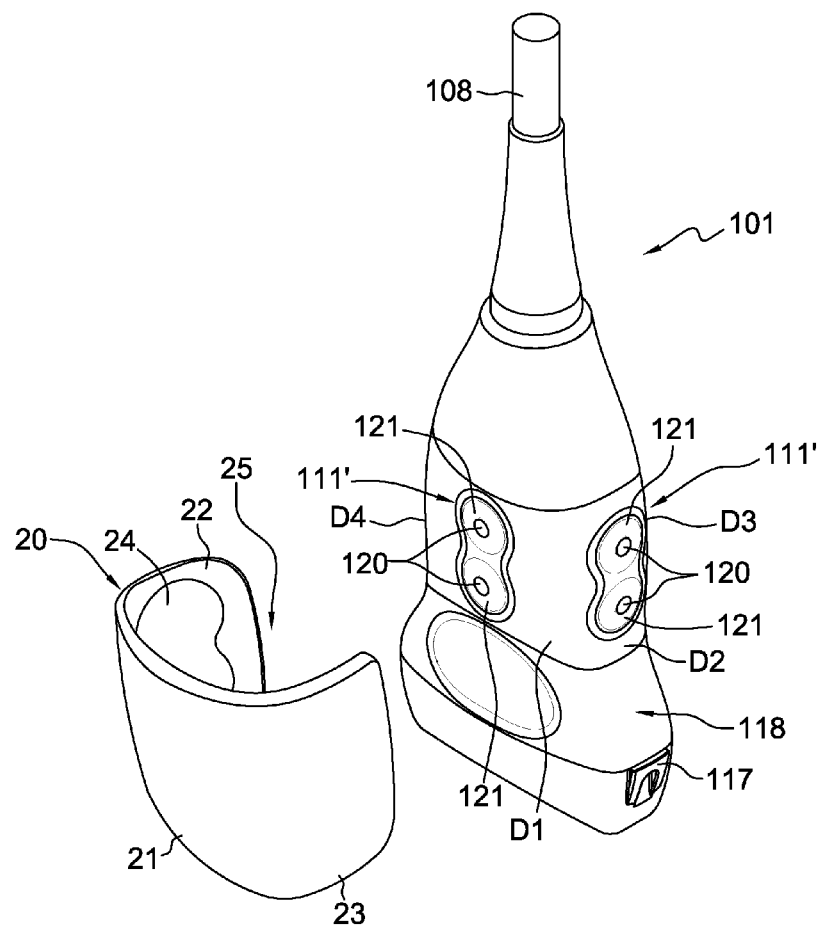
FIG. 12 is a perspective view illustrating an ultrasonic probe and a probe cover according to a second embodiment.

As illustrated in FIG. 12, switches 111' provided on the surfaces D1 to D4 of the ultrasonic probe 101 have buttons 120 projecting on the surface of the ultrasonic probe 101. The button 120 is formed in a recess 121. Since the button 120 is formed in the recess 121 as described above, the button 120 covered by a probe cover 20 is not depressed by the probe cover 20, when the later-described probe cover 20 is attached.

The recess 110 and the magnet 112 are not provided on the ultrasonic probe 101 in the present embodiment.

The probe cover 20 according to the present embodiment is formed to have almost a reversed C shape, and includes a wide portion 21 and narrow portions 22 and 23 formed on both ends of the wide portion 21. A part of the narrow portion 22 is cut out to form an exposure window 24. An opening 25 is formed on the probe cover 20 on the portion opposite to the wide portion 21 between the narrow portions 22 and 23.

Figure 13:
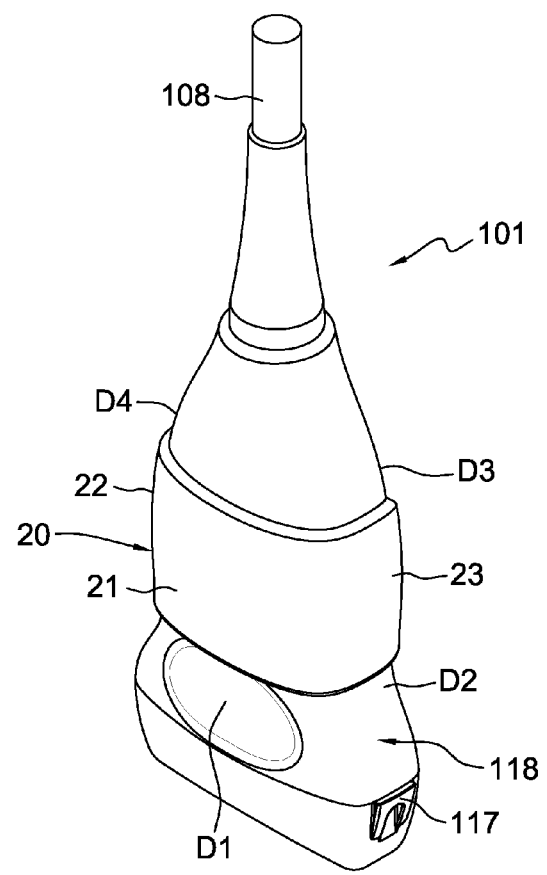
FIG. 13 is a perspective view illustrating the ultrasonic probe to which the probe cover is attached.
Figure 14:
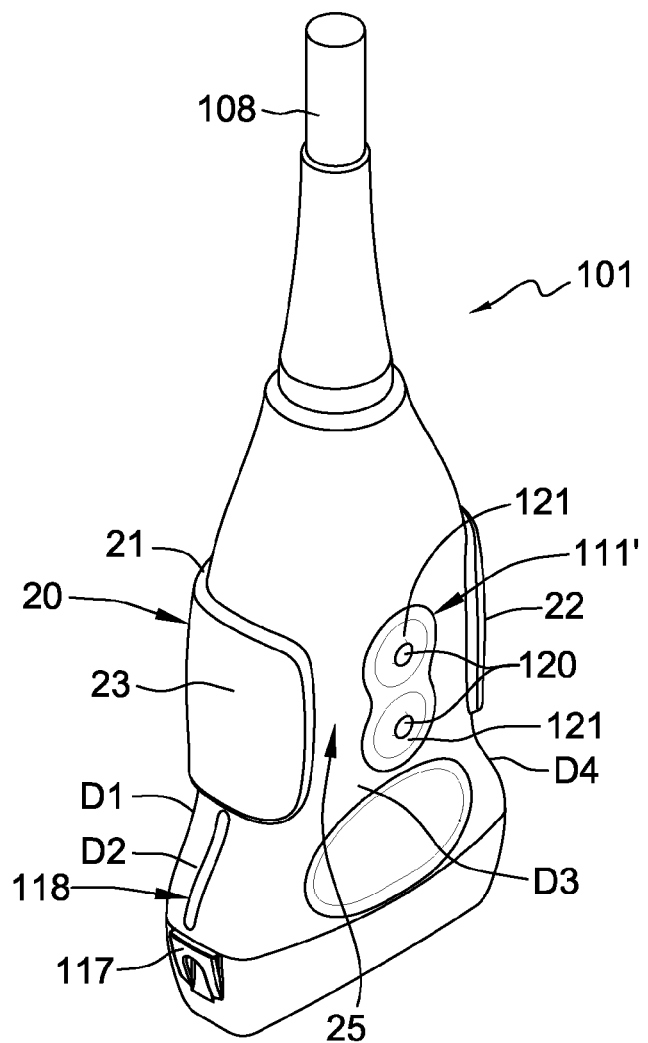
FIG. 14 is a perspective view of the ultrasonic probe illustrated in FIG. 13 as viewed from the reverse side.

The probe cover 20 is made of a hard plastic, for example. As illustrated in FIGS. 13 and 14, the probe cover 20 is fitted and attached to the ultrasonic probe 101. In the present embodiment, the probe cover 20 is also detachable to the ultrasonic probe 101. In the state where the probe cover 20 is attached to the ultrasonic probe 101, the wide portion 21 is located on the wide surfaces D1 or D3 of the ultrasonic probe 101 so as to cover the switch 111'. The narrow portion 23 is located on the narrow surface D2 or D4 of the ultrasonic probe 101 so as to cover the switch 111'.

The narrow portion 22 is located on the narrow surface D2 or D4 of the ultrasonic probe 101. In the ultrasonic probe 101 to which the probe cover 20 is attached, the switch 111' provided on the surface D2 or D4 on which the narrow portion 22 is located is exposed from the exposure window 24. The exposure window 24 is one example of an embodiment of an opening portion.

The opening 25 of the probe cover 20 attached to the ultrasonic probe 101 is located on the wide surface D1 or D3. With this state, the switch 111' provided on the surface D2 or D4 on which the opening 25 is located is exposed from the opening 25. The opening 25 is one example of an embodiment of an opening portion.

Figure 15:
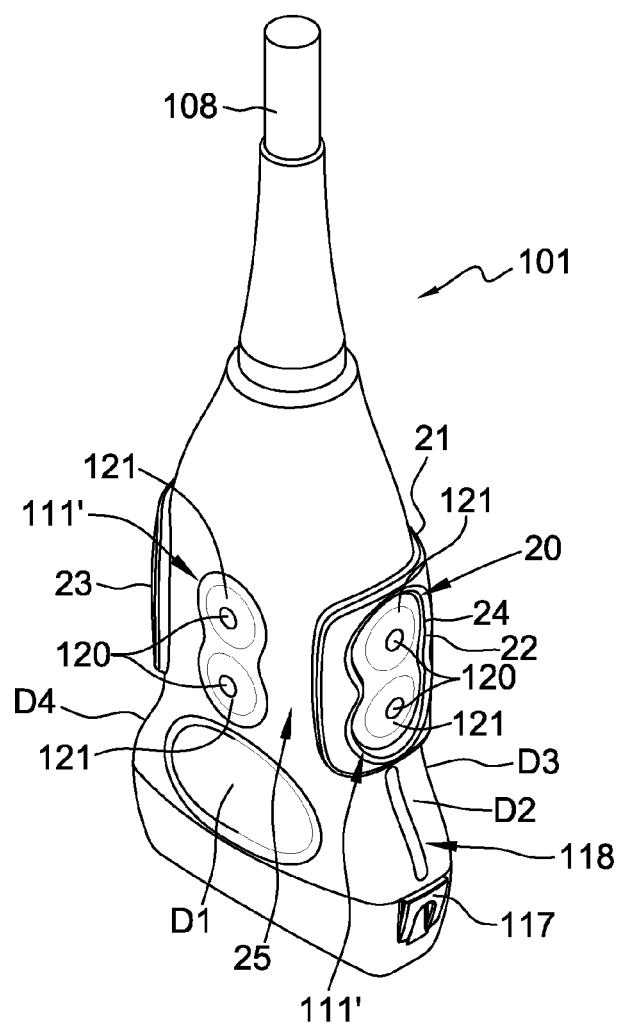
FIG. 15 is a perspective view illustrating the ultrasonic probe to which the prove cover is attached.

When an ultrasonic scan is performed by use of the ultrasonic probe 101 according to the present embodiment, the probe cover 20 is attached to the ultrasonic probe 101 as illustrated in FIGS. 13, 14, and 15. For example, FIGS. 13 and 14 illustrate that the operator holds the ultrasonic probe 101 with his/her left hand, while FIG. 15 illustrates that the operator holds the ultrasonic probe 101 with his/her right hand.

Specifically, the probe cover 20 is attached to the surfaces D1, D2, and D4 of the ultrasonic probe 101 in FIGS. 13 and 14. With this structure, the switches 111' provided on the surfaces D1 and D2 are covered by the wide portion 21 and the narrow portion 23 of the probe cover 20, while the switches 111' provided on the surfaces D3 and D4 are exposed from the opening 25 and the exposure window 24 (not illustrated in FIGS. 13 and 14).

In FIG. 15, the probe cover 20 is attached to the surfaces D2, D3, and D4 of the ultrasonic probe 101. With this structure, the switches 111' provided on the surfaces D1 and D2 are exposed from the opening 25 and the exposure window 24 of the probe cover 20, while the switches 111' provided on the surfaces D3 and D4 are covered by the wide portion 21 and the narrow portion 23.

In the present embodiment described above, the probe cover 20 is attached to the ultrasonic probe 101 in order that the switch 111' that is easy to be depressed by the operator with his/her hand holding the ultrasonic probe 101 is exposed from the exposure window 24 and the opening 25. According to the present embodiment, the position of the switch 111' that can be used can be changed by changing the position of attaching the probe cover 20, whereby the switch 111' that can be used can be located on the position in which the operator can easily operate the switch 111' with his/her right hand and on the position in which the operator can easily operate the switch 111' with his/her left hand. On the other hand, the switch 111' that is not used is covered by the probe cover 20, which can prevent the switch 111' from involuntarily being depressed.

Third Embodiment

A third embodiment will next be described. The components same as those in the first embodiment and the second embodiment are identified by the same numerals.

Figure 16:
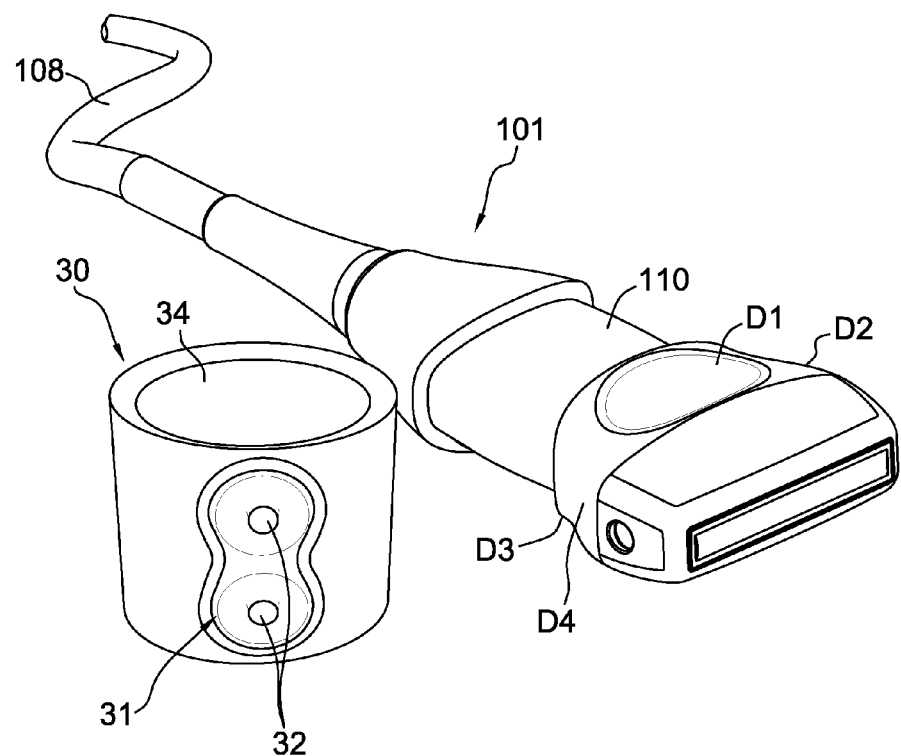
FIG. 16 is a perspective view illustrating an ultrasonic probe and a probe cover according to a third embodiment.
Figure 17:
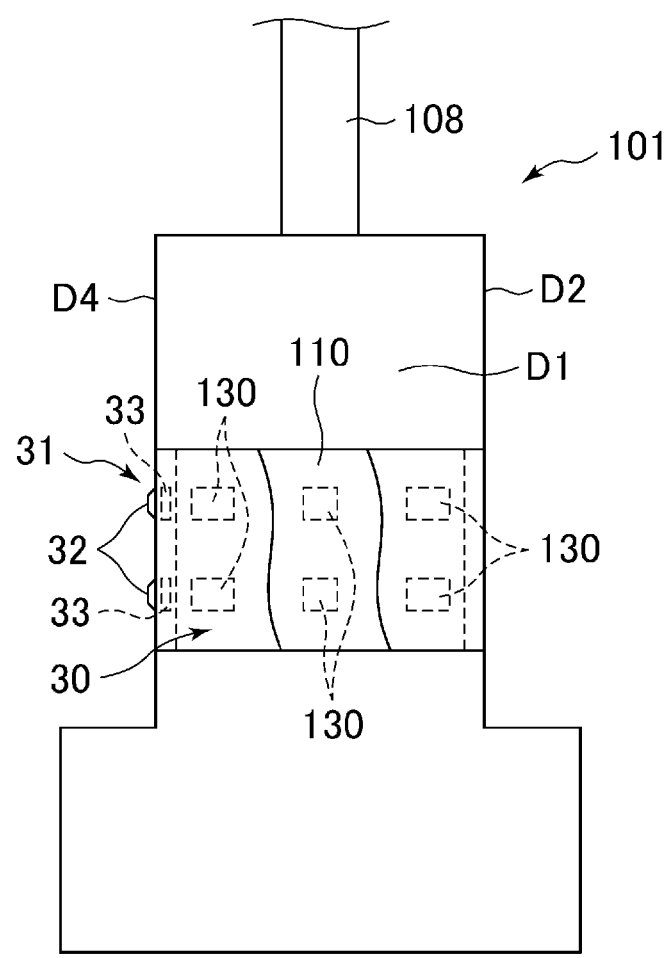
FIG. 17 is a perspective view illustrating the ultrasonic probe illustrated in FIG. 16 to which the probe cover is attached.

In the present embodiment, a probe cover 30 is detachably attached to the recess 110 formed on the ultrasonic probe 101 as illustrated in FIG. 16. The switch 111 is not provided on the ultrasonic probe 101, but as illustrated in FIG. 17, a detection portion 130 detecting that a later-described switch 31 provided on the probe cover 30 is operated is provided. FIG. 17 is a simplified diagram of the ultrasonic probe 101.

Four detection portions 130 are provided in the ultrasonic probe 101 in the vicinity of the respective surfaces D1 to D4 (only three are illustrated in FIG. 17). The detection portion 130 is made of a coil, for example. The detection portion 130 is one example of an embodiment of a detection portion.

The probe cover 30 is annularly formed from a material that is elastically deformed, as in the modification of the first embodiment. The probe cover 30 has a switch 31. The switch 31 is used to input an instruction of the operator to the ultrasonic probe 101. Only one switch 31 is provided, and it has a button 32 projecting on the surface of the probe cover 30. The operator inputs an instruction by depressing the button 32. The switch 31 is one example of an embodiment.

Permanent magnets 33 are provided in the probe cover 30 (FIG. 17). The permanent magnets 33 are provided immediately below the buttons 32. The permanent magnets 33 move through the depression of the buttons 32, whereby induced current flows due to the change in the magnetic field of the coil forming the detection portion 130. Thus, the depression of the switch 31 is detected.

Figure 18:
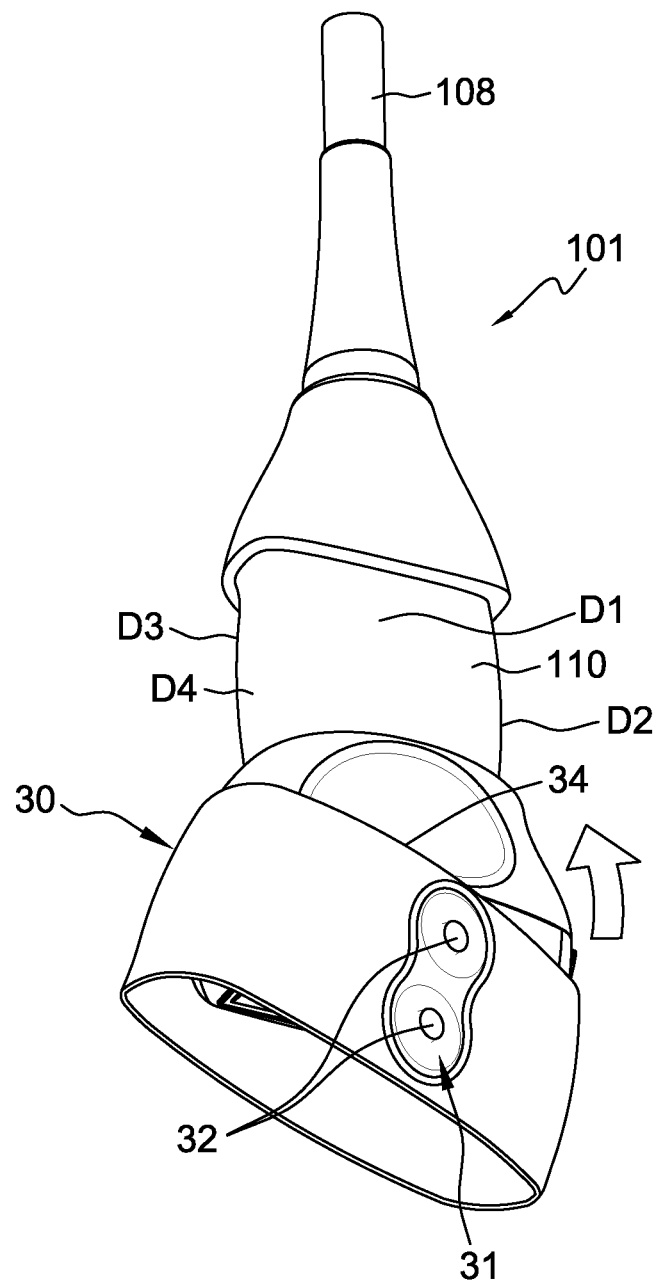
FIG. 18 is a perspective view illustrating the ultrasonic probe to which the probe cover is attached.

When the ultrasonic scan is performed by use of the ultrasonic probe 101 according to the present embodiment, the probe cover 30 is put on the ultrasonic probe 101 from the opening 34 due to the elastic deformation of the probe cover 30, and attached to the recess 110, as illustrated in FIG. 18. In the present embodiment, the probe cover 30 is attached in order that the switch 31 is located immediately above the detection portion 130 on the surface that is easy to be depressed by the operator with his/her hand holding the ultrasonic probe 101. The permanent magnet 33 is located immediately above the detection portion 130 by the attachment of the probe cover 30 as described above, whereby induced current caused by the movement of the permanent magnet 33 can be generated on the detection portion 130 through the depression of the button 32. In FIG. 17, the switch 31 is located immediately above the detection portion 130 on the surface D4.

According to the third embodiment described above, the probe cover 30 can be attached to the ultrasonic probe 101 in such a manner that the switch 31 is located on a desired position. Accordingly, the switch 31 that can be used can be located on the position in which the operator can easily operate the switch 31 with his/her right hand and on the position in which the operator can easily operate the switch 31 with his/her left hand. On the other hand, since only the switch that is to be used is provided on the probe cover 30, there is no chance that the switch is involuntarily depressed.

Figure 19:
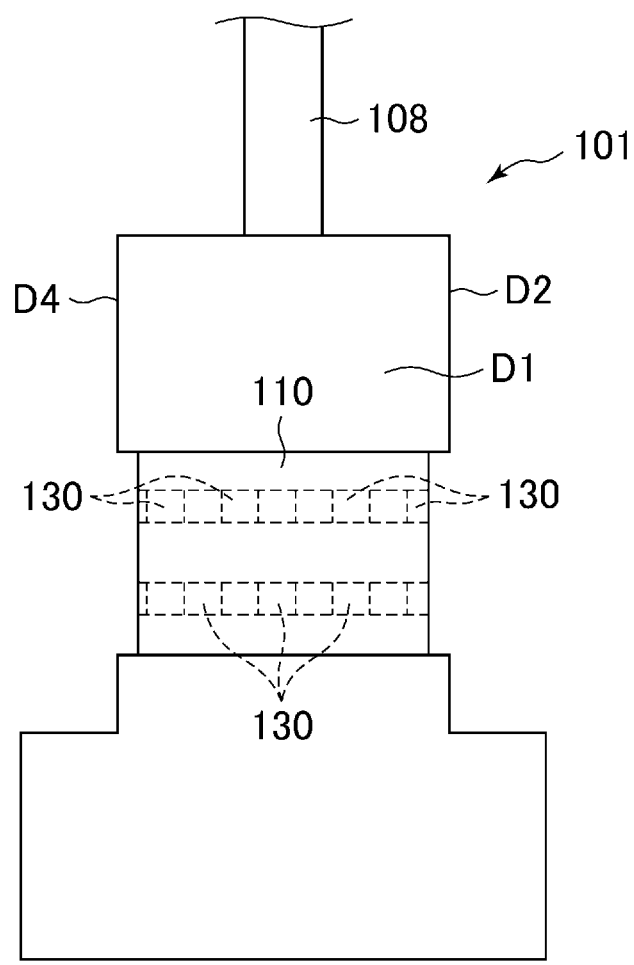
FIG. 19 is a view illustrating another example of an ultrasonic probe according to the third embodiment.

Exemplary embodiments have been described above. The methods and systems described herein can be modified without departing from the scope of the present invention. For example, in the third embodiment, plural detecting portions 130 made of a coil may be provided all over the circumference of the ultrasonic probe 101 as illustrated in FIG. 19. In this case, the probe cover 30 can be attached without restriction in the position of the switch 31 by the position of the detecting portion 130.

In the third embodiment, a coil may be provided on the probe cover 30 instead of the permanent magnet 33 in order that induced current may be flown on the detection portion 130 through the depression of the switch 31. In this case, a power source such as a battery is provided on the probe cover 30 for flowing current through the coil provided on the probe cover 30. Instead of the permanent magnet 33 or the coil, a transmission circuit that generates a signal indicating that the switch 31 is depressed and that wirelessly transmits this signal to the ultrasonic probe 101 may be provided on the probe cover 30. In this case, a reception circuit that receives the signal transmitted from the transmission circuit is provided on the ultrasonic probe 101 as the detection portion 130.

What is claimed is:

1. A probe cover configured to be detachably attached to an ultrasonic probe and cover plural switches on a surface of the ultrasonic probe, the probe cover comprising:
   a depression portion by which an operator can depress at least one switch of the plural switches when the probe cover is attached to the ultrasonic probe; and
   a covering portion that comprises a piece of material configured to cover at least one other switch of the plural switches when the probe cover is attached to the ultrasonic probe, the piece of material positioned and structured such that the operator cannot depress the at least one other switch regardless of whether the at least one switch is depressed;
   wherein the probe cover is configured to be detachably attached to the ultrasonic probe in either a first position or a second position, where, in the first position, the depression portion is positioned on a first one of the plural switches and the covering portion is positioned on a second one of the plural switches, and where, in the second position, the depression portion is positioned on the second one of the plural switches and the covering portion is positioned on the first one of the plural switches.

2. A probe cover according to claim 1, wherein the depression portion is elastically deformable to facilitate depressing the at least one switch of the plural switches.

3. A probe cover configured to be detachably attached to an ultrasonic probe and cover plural switches on a surface of the ultrasonic probe, the probe cover comprising:
   an opening portion configured to expose at least one switch of the plural switches; and
   a covering portion that comprises a piece of material configured to cover at least one other switch of the plural switches when the probe cover is attached to the ultrasonic probe, the piece of material positioned and structured such that the operator cannot depress the at least one other switch regardless of whether the at least one switch is depressed;
   wherein the probe cover is configured to be detachably attached to the ultrasonic probe in either a first position or a second position, where, in the first position, the opening portion is positioned on a first one of the plural switches and the covering portion is positioned on a second one of the plural switches, and where, in the second position, the opening portion is positioned on the second one of the plural switches and the covering portion is positioned on the first one of the plural switches.

4. A probe cover according to claim 1, wherein the plural switches are operation switches configured to input an operator's instruction.

5. A probe cover according to claim 2, wherein the plural switches are operation switches configured to input an operator's instruction.

6. A probe cover according to claim 3, wherein the plural switches are operation switches configured to input an operator's instruction.

7. An ultrasonic probe to which the probe cover according to claim 1 is attached.

8. An ultrasonic probe according to claim 7, wherein a first set of the plural switches are formed at a position on the ultrasonic probe such that an operator can operate the first set of the plural switches with his/her right hand, and a second set of the plural switches are formed at a position on the ultrasonic probe such that an operator can operate the second set of the plural switches with his/her left hand.

9. A probe cover according to claim 1, wherein the probe cover comprises at least one magnet configured to attach the probe cover to the ultrasonic probe.

10. A probe cover according to claim 1, wherein the probe cover comprises two members that each comprise a first portion and a second portion that is oriented generally orthogonal to the first portion.

11. A probe cover according to claim 1, wherein the depression portion comprises at least one convex portion and at least one projecting portion.

12. A probe cover according to claim 1, wherein the probe cover is elastically deformable.

13. A probe cover according to claim 3, wherein the probe cover comprises a middle portion extending between two wing portions that are each oriented generally orthogonal to the middle portion.

14. An ultrasonic probe according to claim 7, wherein the ultrasonic probe comprises at least one magnet configured to attach the probe cover to the ultrasonic probe.

15. A probe cover according to claim 1, wherein the piece of material is a hard plastic.

16. A probe cover according to claim 3, wherein the piece of material is a hard plastic.

* * * * *